(12) United States Patent
Inganäs et al.

(10) Patent No.: US 7,331,969 B1
(45) Date of Patent: Feb. 19, 2008

(54) MICRO TOOLS

(75) Inventors: Olle Inganäs, Linköping (SE); Edvin Jager, Linköping (SE); Anders Selbing, Linköping (SE)

(73) Assignee: Micromuscle AB, Linkoping (SE)

( * ) Notice: Subject to any disclaimer, the term of this patent is extended or adjusted under 35 U.S.C. 154(b) by 718 days.

(21) Appl. No.: 10/018,985

(22) PCT Filed: Jun. 18, 2000

(86) PCT No.: PCT/SE00/01286

§ 371 (c)(1),
(2), (4) Date: Dec. 19, 2001

(87) PCT Pub. No.: WO00/78222

PCT Pub. Date: Dec. 28, 2000

(51) Int. Cl.
*A61B 17/10* (2006.01)
*A61B 17/128* (2006.01)

(52) U.S. Cl. ................ 606/143; 606/142; 606/151; 606/157

(58) Field of Classification Search ............ 606/1, 606/108, 138–200, 205–211, 222–233; 604/19, 604/22, 507, 508, 164.01, 264, 272, 523; 623/1.1, 1.11, 1.18, 1.19, 1.21, 2.1, 11.11
See application file for complete search history.

(56) References Cited

U.S. PATENT DOCUMENTS

| 5,634,913 | A | * | 6/1997 | Stinger | 604/272 |
|---|---|---|---|---|---|
| 5,771,902 | A | * | 6/1998 | Lee et al. | 128/897 |
| 5,819,749 | A | | 10/1998 | Lee et al. | |
| 5,855,565 | A | | 1/1999 | Bar-Cohen et al. | |
| 6,102,897 | A | * | 8/2000 | Lang | 604/246 |
| 6,587,250 | B2 | * | 7/2003 | Arngarth et al. | 359/265 |
| 6,663,821 | B2 | * | 12/2003 | Seward | 264/512 |
| 2003/0236445 | A1 | | 12/2003 | Couvillon, Jr. | |

FOREIGN PATENT DOCUMENTS

| SE | SE 9500849-6 | 3/1995 |
|---|---|---|
| WO | WO 96/28841 | 9/1996 |
| WO | WO 97/39674 | 10/1997 |
| WO | WO 97/39688 | 10/1997 |
| WO | WO 98/37816 | 9/1998 |
| WO | WO 2007/015675 A1 | 2/2007 |

OTHER PUBLICATIONS

Controlled Folding of Micrometer-Size Structures; By: Elisabeth Smela, Olle Inganas and Ingemar Lundstrom; Science vol. 268, Jun. 23, 1995 pp. 1735-1738.

(Continued)

*Primary Examiner*—Glenn K. Dawson
(74) *Attorney, Agent, or Firm*—Harness, Dickey & Pierce, PLC

(57) ABSTRACT

Tool arrays for biomedical surgery where the tools consist of layered polymer micromuscles arranged to induce geometrical changes and movements via an electrochemically induced change of volume in at least one polymer layer. The tool or tool arrays are mounted on a carrier having the form of a needle being inserted into a cannula/catheter through which the tools can be electrically actuated via external means to induce a mechanical movement to act upon biological structures.

18 Claims, 5 Drawing Sheets

OTHER PUBLICATIONS

"Electroactive Polymers (EAP) Actuators as Artificial Muscles—Reality, Potential, and Challenges" 2nd ed. Y. Bar-Cohen (ed.) ISBN 0-8194-5297-1.

Q. Pei and O. Inganäs, "Conjugated polymers and the bending cantilever method: electrical muscles and smart devices," Advanced materials, 1992 4(4) p. 277-278.

"Controlled Folding of Micron-size Structures", Science 268 (1995) pp. 1735-1738) or only polymer layers, Elisabeth Smela, Olle Inganäs and Ingemar Lunström.

"Controlled Delamination Materials—Using Electrochemistry to Break Adhesive Joints in the Packaging Industry", Karlstad University, Department of Physics, Karlstad, Sweden, Danielsson, C-O.

"Controlled Delamination of Adhesives within Packaging and Distribution", Danielsson, C-O, Norberg, P. and Sandberg, L.

Jager et al., "Microfabricating Conjugated Polymer Actuators", Science 2000 290: 1540-1545.

"Electroactive Polymers (EAP) Actuators as Artificial Muscles—Reality, Potential, and Challenges" 2nd ed. Y. Bar-Cohen (ed.) ISBN 0-8194-5297-1.

Q. Pei and O. Inganäs, "Conjugated polymers and the bending cantilever method: electrical muscles and smart devices," Advanced materials, 1992 4(4) p. 277-278.

"Controlled Folding of Micron-size Structures", Science 268 (1995) pp. 1735-1738) or only polymer layers, Elisabeth Smela, Olle Inganäs and Ingemar Lunström.

"Controlled Delamination Materials—Using Electrochemistry to Break Adhesive Joints in the Packaging Industry", Karlstad University, Department of Physics, Karlstad, Sweden, Danielsson, C-O.

"Controlled Delamination of Adhesives within Packaging and Distribution", Danielsson, C-O, Norberg, P. and Sandberg, L.

Jager et al., "Microfabricating Conjugated Polymer Actuators", Science 2000 290: 1540-1545.

* cited by examiner

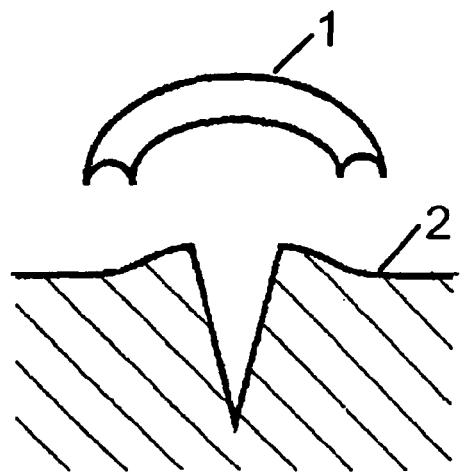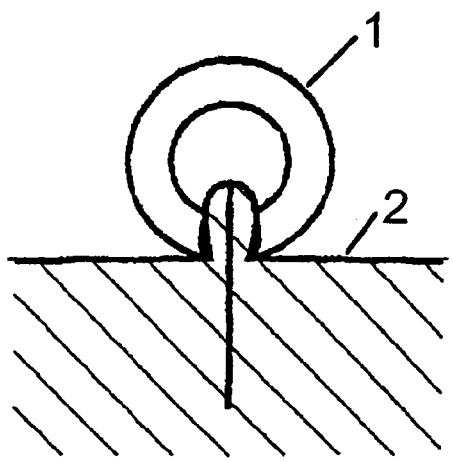
Fig 1a  Fig 1b
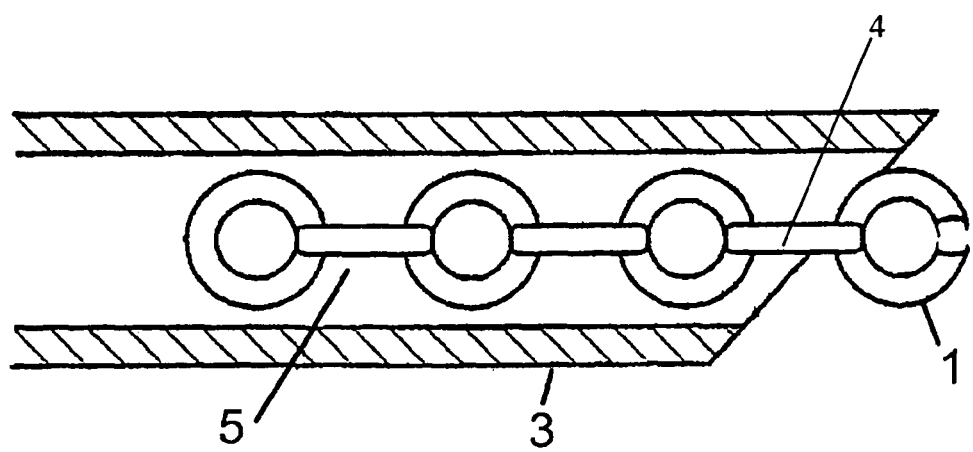
Fig 1c

MICRO TOOLS

TECHNICAL FIELD

This invention concerns micro-surgical tools that can be delivered by a catheter or needle. These tools or microstructures can be used to adapt, assemble, separate, fortify, dilate, close and hold biological structures inside the body during and after surgery. The tools may be stents, valves, clips, nets, knives, scissors, dilators, clamps, tweezers etc.

BACKGROUND OF THE INVENTION

The use of microstructures to assemble, fortify or dilate biological structures inside the body during and after surgery can help the surgeon in a number of ways. The operation of electrically actuated tools can help the surgeon to simultaneously position, operate manually, and observe. By positioning the tool by hand and separately operating the tool through external controls (i.e. footswitch, voice control, other software-control) a much higher degree of precision is achieved. In microsurgery, this is especially desired.

The development of microactuators has been spurred on by the desire to be able to use tools beforehand or during invasive surgical procedures. Because tools may be used for cutting, drilling, holding, dilating, suturing, adapting or supporting, the tools must have specific size and shape. For example, a certain tool might be need during a surgery and the only way to introduce this tool is to place it inside a catheter or needle. Thus, the tool must designed within the specific dimension of the catheter or needle.

The necessary elements to accomplish these functions are the electrochemically activated microactuators, built by micromachining thin metal and polymer layers or only polymer layers. (Elisabeth Smela, Olle Inganäs and Ingemar Lundström: "Controlled Folding of Micron-size Structures", Science 268 (1995) pp. 1735-1738) or only polymer layers. These microactuators can be produced in sizes from micrometers to centimeters, and operate well in biological fluids such as blood plasma, blood, buffer and urine. They are therefore suitable tools for micro invasive surgery inside the body. The versatility of construction and the speed of response, as well as the force of these microactuators render them as one of the best types of microactuators inside the body. An international patent covers one route of fabrication of such devices (A Elisabeth Smela, Olle Inganäs and Ingemar Lundström: "Methods for the fabrication of micromachined structures and micromachined structures manufactured using such methods", Swedish patent application number SE 9500849-6, Mar. 10, 1995 in succession also a PCT and international patent).

The combination of microactuators and catheters are not well documented in the literature. No patents describe the use of microactuators as tools housed inside a catheter; however several examples of microactuators used to position a catheter are to be found in the following patents:

U.S. Pat. No. 5,771,902 Micromachined actuators/sensors for intratubular positioning/steering U.S. Pat. No. 5,519,749 Microvalve WO9837S16A1 Microfabricated therapeutic actuators WO9739688A2 Method and apparatus for delivery of an appliance in a vessel WO9739674A1 Spring based multi-purpose medical instrument U.S. Pat. No. 5,855,565 Cardiovascular mechanically expanding catheter Several mechanisms are suggested for the microactuators in these applications, found among shape memory alloys (including polymeric materials) and piezoelectric materials. The use of conjugated polymers in micromuscles is not documented for catheter tools.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIGS. 1A-1C are a perspective view of the first embodiment of the present invention.

DETAILED DESCRIPTION OF INVENTION

Figure 2:
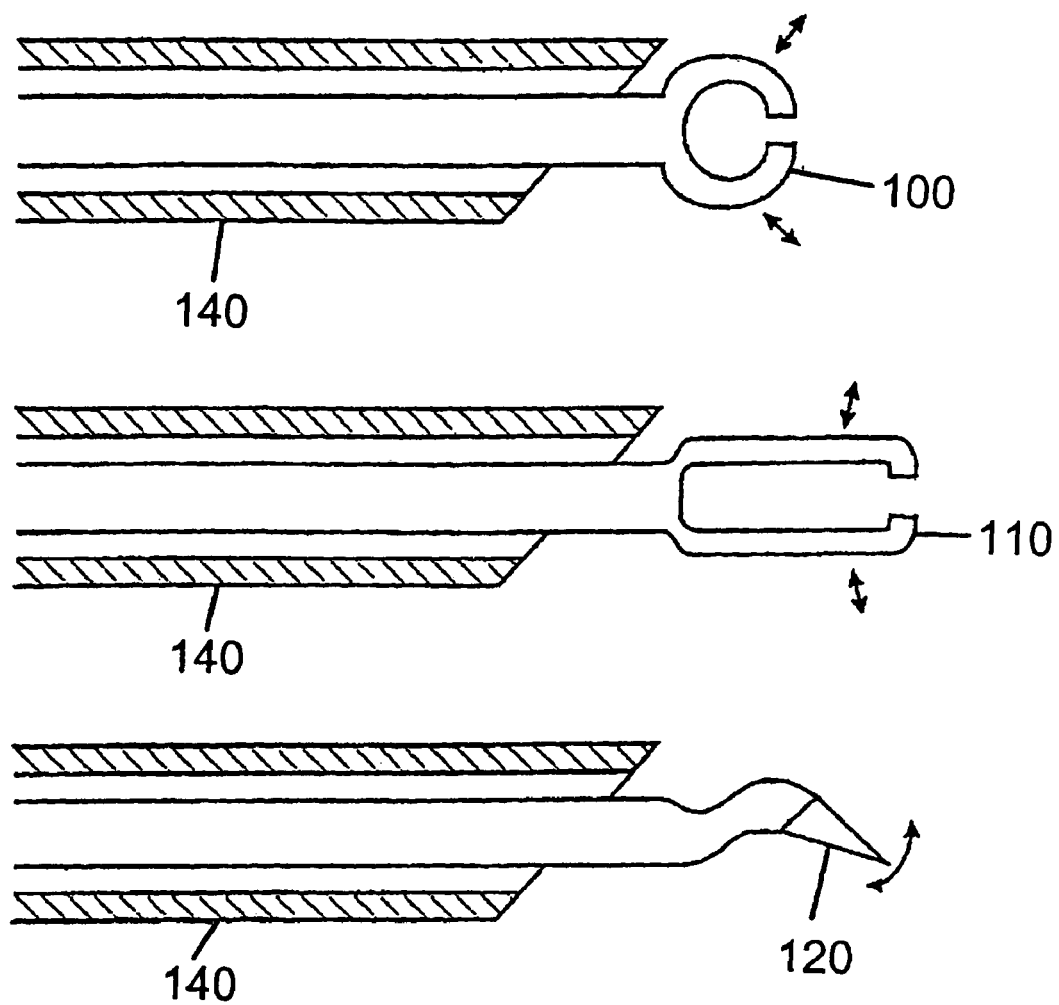
FIG. 2 is a perspective view of other tools in which microactuators are used.

Our novelty and innovation resides in the use of microactuators based on conjugated polymers being electrically operated and mounted in or on a catheter or needle. These microactuators are positioned with the help of the catheter, and then activating these microactuator structures that are carried on the needle. The microfabrication of such microactuators renders possible a number of geometries and a size as small as ~10 μm, which is difficult to produce by mechanical production techniques. They may be produced by use of the method presented in SE 9500849-6 above and then mounted in or on the needle or catheter, or they might be produced by novel manufacturing methods. With the invention described therein, completely novel microsurgery tools are now available.

More particularly, in accordance with the present invention there is provided a tool array for biomedical surgery, comprising:

(i) a plurality of tools each comprising layered polymer microactuators arranged to induce geometrical changes and movements via an electrochemically induced change of volume in at least one polymer layer, and (ii) the tools being arranged as an array of tools mounted in a carrier having the form of a catheter through which the tools can be electrically actuated via externally to induce a mechanical movement to act upon biological structures.

The introduction of structures in or through a catheter or needle is of particular interest and more specifically the application of tools, which are to be left at the site after insertion, and which have to execute their function for some limited time duration. The production of individually actuated tool arrays render little difficulty beyond producing the individual tool. Electrical contacts must be supplied to actuate each microactuator separately. This can be done by wiring the single microactuator to be used as the working electrode; the catheter is then used as the counterelectrode, and will supply all the charge that is needed to actuate all those microactuators. As wires may easily be produced in width down to 10 μm with photolithography or with soft lithography, thus by putting down parallel conductor wires 50 microactuators at least may be placed along the tool array located in/on a needle of 1 mm width. Should more wires be necessary, more elaborate addressing schemes might be used.

If a three electrode system is necessary in any application, microfabricated reference electrodes or macrosize reference electrodes carried on the catheter housing can be used as a third electrode.

A first embodiment of the present invention is clips used for surgery. These clips are sub-millimeter to millimeter structures, used to hold two separated biological structures joined, for example during a healing period. FIG. 1A-1C shows an example of a clip tool in which microactuator may be used. Clips may be used in surgery to hold together two separate biological structures. FIG. 1A-FIG. 1B show a clip 1 before and after it is used to join the structure 2 to hold it closed. The clip 1 is attached to second clip 4 and a chain of clips 5 that are confined by a cylindrical housing 3, as shown in FIG. 1C. The cylindrical housing 3 may be catheter or a needle.

Another embodiment is a structure for controlling the flow through blood vessels. The simplest example is that of a clip used to prevent blood flow to a biological structure downstream in the blood vessel. Such a clip, or series of clips, would be mounted and left to hold a firm grip on the blood vessel and thus to prevent the flow of blood. In FIG. 1c is shown a series of structures suitable for constricting blood vessels. This array of tools may only be collectively addressed, and the tool array is designed to set free the outermost clip, on actuation of all the clips 5, a mechanism of confining the movements of all but the outermost clip is needed. This is done by assembling the clip array 5 into a cylindrical housing 3, preferably a catheter, prior to insertion in the body. The cylindrical housing 3 confines the motion of microactuators, which search in vain to expand the strong metal casing on operation. When the outermost clip 1 is actuated, the clip is opened; likewise is the next-to-the outermost clip 4 partially free to move as it is protruding outside the cylindrical housing. Therefore the partial opening of the next-to-the outermost clip 4 sets the outermost clip 1 free, as well as opens it up for subsequent spontaneous closing the site to be clipped.

FIG. 2 shows tubular tweezers 100, tweezers 110, knifes 120, based on microactuators. The indicated movement is driven by microactuators properly mounted and designed. The tools are housed in a cylindrical housing 140, which, for example, may be a needle or a catheter.

Figures 3A, 3B:
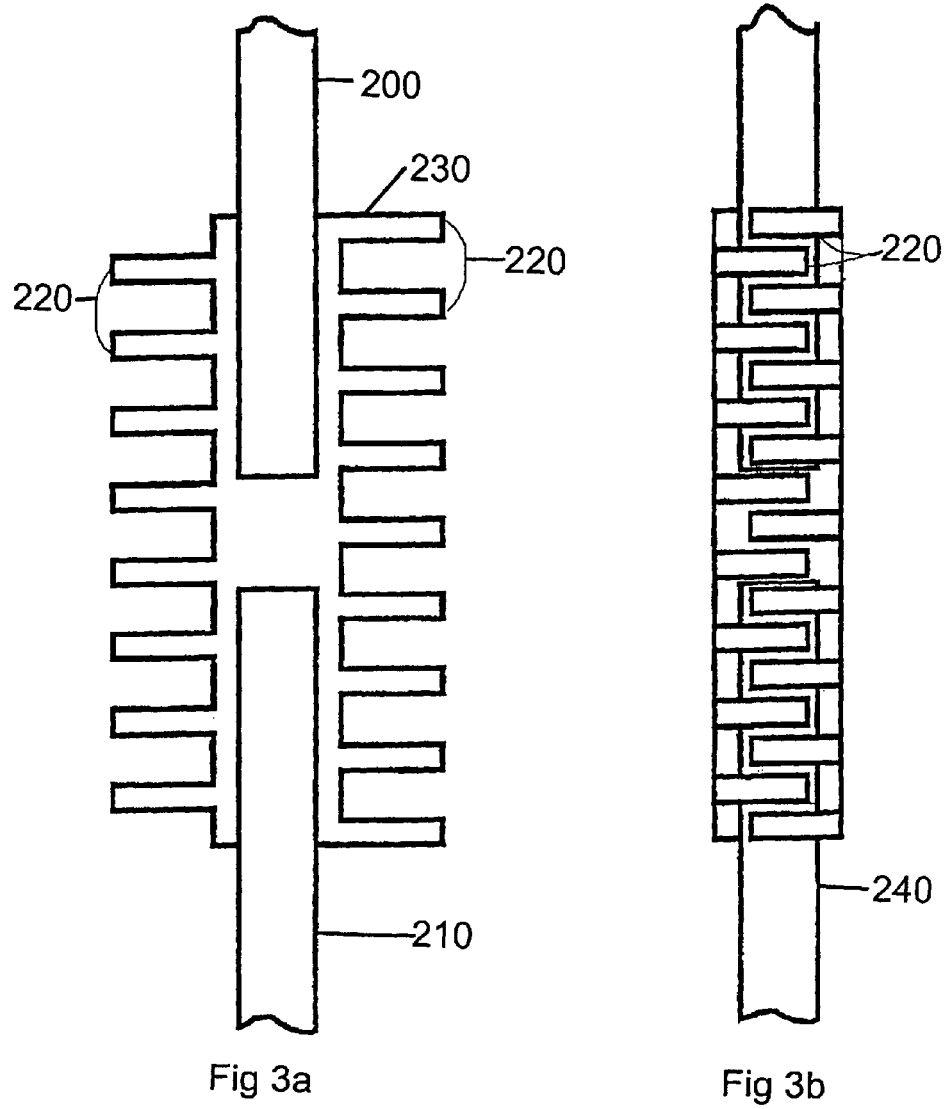
FIGS. 3A-3B are a perspective view of the fifth embodiment of the present invention.

FIGS. 3A-3B show a fifth embodiment 230 of the present invention. Arrays of fingers could be used to hold cylindrical objects, such as nerves and nerve fibers, or blood vessels. With the help of microactuators holding the structures (FIG. 3A-3B), adjacent microstructures can operate as neural sensing or activating electrodes, and will enable recording of signals from or to activate nerves. Furthermore, they could be used as a synthetic neural connector, or bridging a severed nerve or nerve fiber. A neural connector 230, with a number of small fingers 220 coil around two cylindrical nerves 200, 210 to tightly hold the nerve 240. Two separate nerves 200, 210 are here joined with the help of a common neural connecter 230. This procedure is used to regrowth the nerves. In addition, small electrodes (not shown) can be fashioned along with the microfingers 220, and be used to sense or excite nerve signals.

Figure 4A:
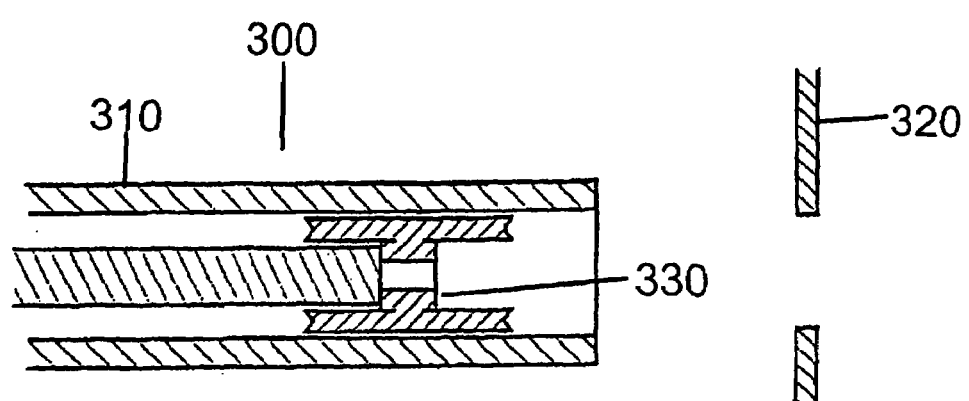
FIGS. 4A-4B are a perspective view of the sixth embodiment of the present invention.
Figure 4B:
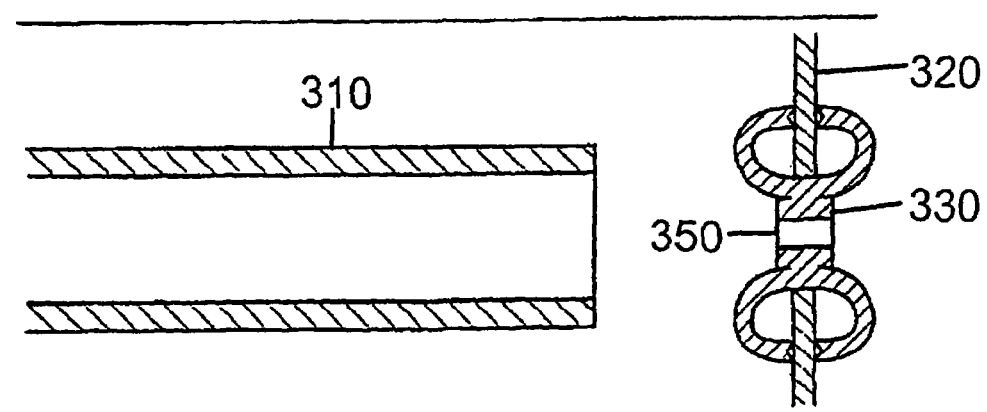

Tools with some temporary mechanical function could also be inserted in membranes (FIG. 4A-4C). Insertion devices with temporary mechanical functions could be used for mounting a hole through a membrane commonly used in ear surgery for pressure equilibration. Making these tools as microdevices will decrease the effort to place and remove the inserted devices and to keep them in place during the desired time period. FIGS. 4A-4C show a sixth embodiment 300 of the present invention. An insertion device 330, for making a temporally hole in a membrane 320 permanent is housed in a catheter/cannula/needle 310 and is inserted through the membrane 320 so as to make the device 330 form a hole 350 through the membrane.

Figure 5A:
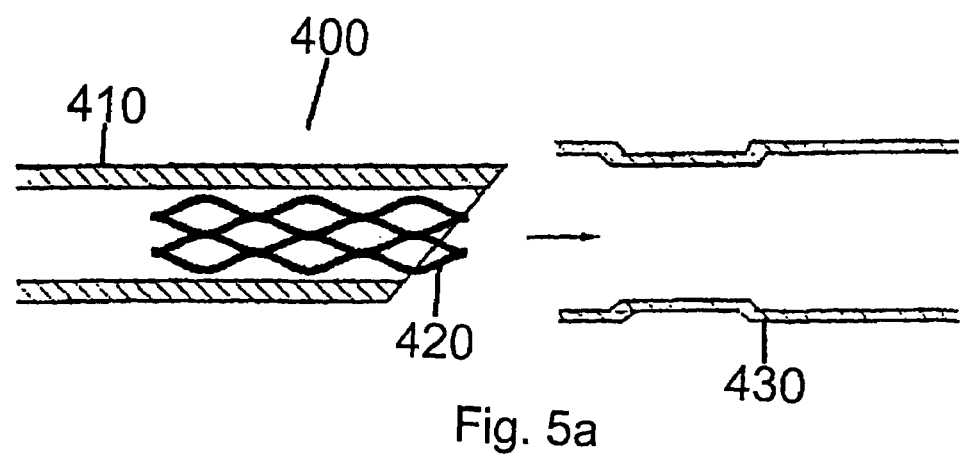
FIGS. 5A-5B are a perspective view of the seventh embodiment of the present invention.
Figure 5B:
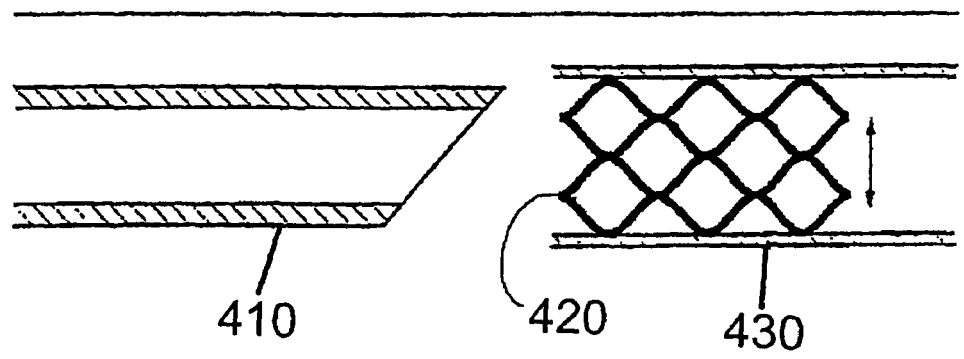

FIGS. 5A-5B show a stent device. The seventh embodiment 400 is somewhat more complex with structures built with a geometry where they could be used inside or outside tube-like structures 410, i.e. stents 420 to dilate a stenotic area 430 or to internally or externally fortify or join the structure(s) (FIGS. 5A and 5B). Stents 420 are of particular interest since they are inserted inside the tube 410, then they are left there to expand a stenotic (examples: blood vessel, biliary duct) or to fortify a weak (examples: blood vessel with aneurysm, divided biliary duct) part of a tubular structure 430 (FIG. 5B).

Clips, stents, finger arrays and insertion devices, once applied, could be reabsorbed or be permanent. They could express various degrees of stimulation of cell growth on its surfaces, various degrees of anti-thrombotic activity, as well as different antibiotic activities. They can also be carriers of various biochemical or biological components.

It should be emphasized that the above-described embodiments of the present invention are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

The invention claimed is:

1. A tool array for biomedical surgery, comprising:
   (i) a plurality of tools each comprising layered polymer microactuators arranged to induce geometrical changes and movements via an electrochemically induced change of volume in at least one polymer layer, and
   (ii) said tools being arranged as an array of tools mounted in a carrier having the form of a catheter through which the tools can be electrically actuated via externally to induce a mechanical movement to act upon biological structures.

2. A tool array according to claim 1, characterized in that the layered polymer consists of a single layered polymer.

3. A tool array according to claim 1, characterized in that the layered polymer consists of a bi-layered polymer.

4. A tool array according to claim 1, characterized in that the layered polymer consists of a multilayered polymer and metal layers.

5. A tool array according to claim 1, characterized in that the mechanical movement is used to position a biological structure.

6. A tool array according to claim 1, characterized in that the mechanical movement is used to hold a biological structure.

7. A tool array according to claim 1, characterized in that the mechanical movement is used to fortify a biological structure.

8. A tool array according to claim 1, wherein a number of identical tools are located on the tool array extending inside the catheter, and wherein actuation of a tool closest to an exit of the catheter is arranged to release a tool from the tool array and is arranged to leave it at the point of exit of the catheter in order to mount the tool at/in some biological structure.

9. A tool array according to claim 8, wherein a number of identical tools are located on the tool array extending inside the catheter and where each tool is arranged to become individually actuated.

10. A tool array according to claim 8, characterized in that a number of non-identical tools are located on the tool array extending inside the catheter and where each tool is arranged to become individually actuated.

11. A tool array according to claim 8, characterized in that each individual tool is a clip arranged to join biological tissue or tissue parts, and arranged to hold the said tissue or tissue parts to allow healing.

12. A tool array according to claim 8, wherein the polymer microactuators are built of layers, of which at least one is a conjugated polymer.

13. A tool array according to claim 12, wherein the conjugated polymer is selected from the group consisting of pyrrole, aniline, thiophene, para-phenylene, vinylene, and a phenylene polymer and a copolymer and substituted forms thereof.

14. A tool array according to claim 1, characterized in that an individual tool is a clip arranged to join biological tissues or tissue parts, and arranged to hold the said tissues or issue parts to allow healing.

15. A tool array according to claim 1, wherein the polymer microactuators are built of layers, of which at least one is a conjugated polymer.

16. A tool array according to claim 15, wherein the conjugated polymer is selected from the group consisting of pyrrole, aniline, thiophene, para-phenylene, vinylene, and a phenylene polymer and copolymer, and substituted forms thereof.

17. A tool array according to claim 15, characterized in that the tool is built of bi-layered polymer, where the electrically activated volume change of said, at least one conjugated polymer is arranged to cause a bending of said bi-layer.

18. A tool array according to claim 15, characterized in that the tool is built of multilayered polymer, where the electrically activated volume change of said, at least one conjugated polymer is arranged to cause a bending of said multilayer.

* * * * *

UNITED STATES PATENT AND TRADEMARK OFFICE
CERTIFICATE OF CORRECTION

PATENT NO. : 7,331,969 B1 Page 1 of 1
APPLICATION NO. : 10/018985
DATED : February 19, 2008
INVENTOR(S) : Olle Inganas, Edvin Jager and Anders Selbing It is certified that error appears in the above-identified patent and that said Letters Patent is hereby corrected as shown below:

Please add: Title Page;

(30) Foreign Application Priority Data: June 21, 1999 (SE) ......... 9902348-3

Signed and Sealed this

Twenty-second Day of July, 2008

JON W. DUDAS
*Director of the United States Patent and Trademark Office*